United States Patent [19]
Mayer et al.

[11] Patent Number: 5,900,378
[45] Date of Patent: May 4, 1999

[54] GAS ANALYSIS OF SEALED AMPULES

[75] Inventors: Daniel W. Mayer, Wyoming; Timothy Ascheman, Ramsey, both of Minn.

[73] Assignee: Modern Controls, Inc., Minneapolis, Minn.

[21] Appl. No.: 08/885,537

[22] Filed: Jun. 30, 1997

[51] Int. Cl.⁶ .............................. G01N 1/24; G01N 1/10
[52] U.S. Cl. .................... 436/181; 436/180; 422/68.1; 422/83; 73/19.1; 73/19.12
[58] Field of Search .................... 422/82.04, 83, 422/94, 79, 80, 101; 436/75, 177, 127, 62, 181; 73/19.01, 19.1, 52, 53.01, 61.41, 64.56, 863.21, 863.81, 863.82, 864.21, 864.24, 863.84, 19.12

[56] References Cited

U.S. PATENT DOCUMENTS

| | | |
|---|---|---|
| 2,987,912 | 6/1961 | Jacobson . |
| 3,942,792 | 3/1976 | Topol . |
| 4,351,802 | 9/1982 | Baylis et al. ............................... 422/89 |
| 5,604,297 | 2/1997 | Seiden et al. ....................... 422/68.1 X |

*Primary Examiner*—Elizabeth McKane
*Attorney, Agent, or Firm*—Palmatier, Sjoquist, Voigt & Christensen, P.A.

[57] ABSTRACT

A method for obtaining a gas sample from a sealed glass ampule containing a liquid and a gas, wherein the steps are immersing the sealed glass ampule in water beneath a collection chamber which is also immersed in water, breaking the glass ampule to permit the gas in the ampule to bubble upwardly into the collection chamber, inserting a hollow needle connected to a syringe into the collection chamber to obtain a sample of the bubbled gas, and injecting the obtained sample into a gas analyzer machine.

7 Claims, 2 Drawing Sheets

GAS ANALYSIS OF SEALED AMPULES

BACKGROUND OF THE INVENTION

This invention relates to a process for obtaining gas samples from a sealed glass ampule of the type commonly used in the medical field.

Glass ampules are commonly used in the medical field for preserving medicines of various types in a sealed environment for storage prior to use. At the time of use the ampules are broken at a scored groove in the neck of the glass, and a needle is inserted into the opening so that the medicine may be withdrawn with a syringe. At the time the ampule is prepared for manufacture the ampule has an open glass neck into which a measured amount of a desired liquid medicine may be inserted, and then the open neck of the ampule is heated to the melting point of the glass to cause the neck to form a glass seal, and to therefore enclose the medicine in the sealed glass ampule container. The filling process never completely fills the ampule, always leaving a small volume of gas in the container with the sealed liquid. For this reason, the filling process is completed in an inert gas atmosphere in order to ensure that the medicine will not become contaminated during storage from exposure to oxygen or other contaminating gases; the inert gas most frequently used is nitrogen.

There is a need to provide a quality inspection procedure for the manufacturing process described above, to sample the gas entrapped in the sealed ampule in order to verify that the gas does not contain any substantial quantity of oxygen, in order to confirm that the medicine in the ampule will have an adequate shelf life before use. Unfortunately, because the ampules comprise a sealed glass container, the quality inspection procedure requires that the ampule be broken in order to gain access to the gas contained in the interior, thereby creating a destructive testing process. This means that quality testing can only be done on a sampling basis, wherein random or statistically accurate samples of ampules are withdrawn from the assembly line process for testing. Further, even if a destructive process is used, it is extremely difficult to withdraw a gas sample from the ampule without contaminating the sample.

SUMMARY OF THE INVENTION

The invention comprises a process for withdrawing gas samples from glass ampules, having the steps of immersing the ampule in water beneath a collection chamber, breaking the glass seal of the ampule to permit the gas to escape into the collection chamber, inserting a needle into the collection chamber to retrieve a gas sample from the chamber with a syringe, and injecting the retrieved sample into a commercially available gas analyzer.

It is a principal object of the present invention to obtain a gas sample from a sealed glass ampule without contamination of the sample.

It is another object and advantage of the invention to provide a gas sampling method and process which comprises only a relatively few simple steps, and can be accomplished without expensive special equipment.

Other and further objects and advantages will become apparent from the specification and claims appended hereto, and with reference to the drawings.

DESCRIPTION OF THE PREFERRED EMBODIMENT

Figure 1:
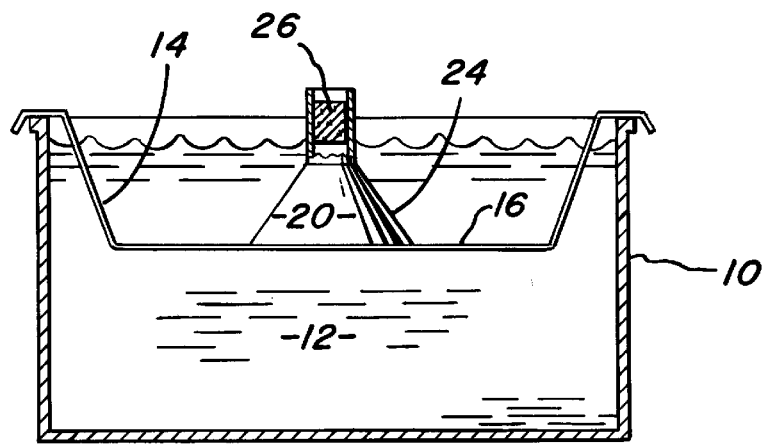
FIG. 1 shows a side cross-section view of the test apparatus.
Figure 2:
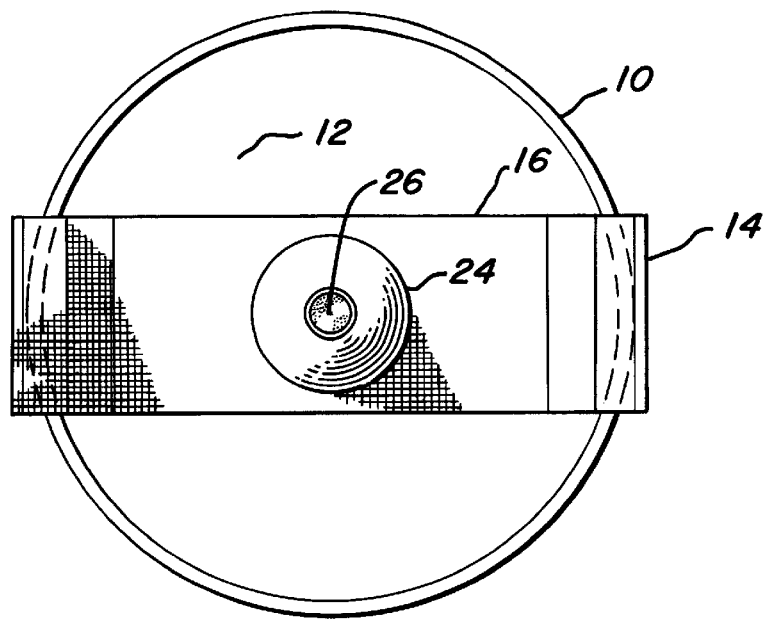
FIG. 2 shows a top view of the test apparatus.

Referring first to FIG. 1 and FIG. 2, the test apparatus is shown in side elevation view in cross section, and in top view. A container 10 is partially filled with water or other suitable liquid 12, and a screen 14 is suspended into the water so as to provide a platform 16 beneath the water surface. The platform 16 preferably is comprised of an open mesh which permits the free flow of water and gas therethrough.

A collection chamber 20 is provided on platform 16, wherein collection chamber is initially completely filled with water. Collection chamber 20 may be conveniently made from an inverted funnel 24, and a rubber stopper 26 may be inserted into the neck end of the funnel after the funnel has been immersed into water 12 to a depth which completely fills chamber 20. Care should be taken to insert the stopper 26 into the neck of the funnel 24 sufficiently far so as to contact the water surface and not leave any air in the top of the chamber 20; it may be necessary to insert a hollow needle/syringe through stopper 26 to withdraw any air entrapped in the top of chamber 20. Another technique for completely filling chamber 20 in funnel 24 is to immerse the funnel 24 in the water in a sideways position, thereby permitting all air in the funnel to escape, and then turning the funnel to an upright position while still immersed in the water to completely fill the chamber 20 with water in the upright position. Using this technique, the stopper 26 is inserted into the funnel neck before the immersion and is not removed.

Figure 3:
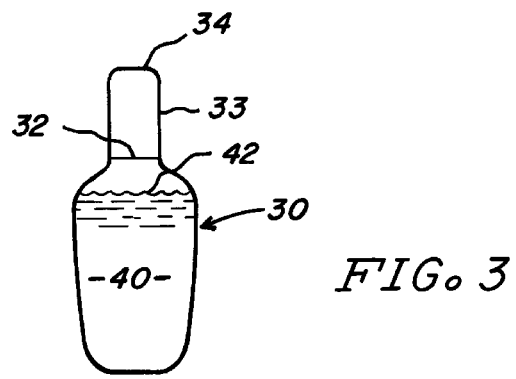
FIG. 3 shows a side view of a typical sealed ampule of the type used in conjunction with the process.

FIG. 3 shows a typical glass ampule 30 with a typical fill of medicine 40 to a level 42. Glass ampule 30 has a scored groove 32 at the base of a neck 33, to facilitate the breaking open of ampule 30 at the time of use. The top end 34 of ampule 30 is typically sealed by melting the glass to close the otherwise open end of ampule 30, after the liquid 40 has been inserted.

Figure 4A:
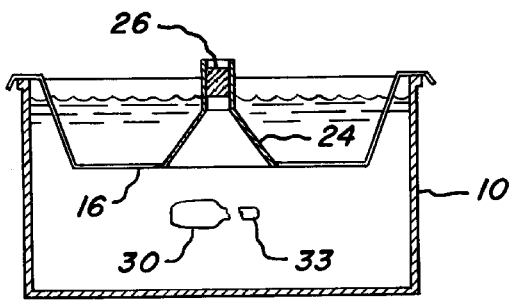
FIG. 4A shows a first process step.

FIG. 4A shows a first step of the process, which occurs after the container 10 has been filled with water and the funnel 24 has been positioned as described above. An ampule 30 is positioned beneath the funnel 24 open end and the ampule 30 is broken at groove 32, whereby the neck 33 is broken away from the lower portion of ampule 30. Because of surface tension effects, this step frequently does not release any gas entrapped in ampule 30.

Figure 4B:
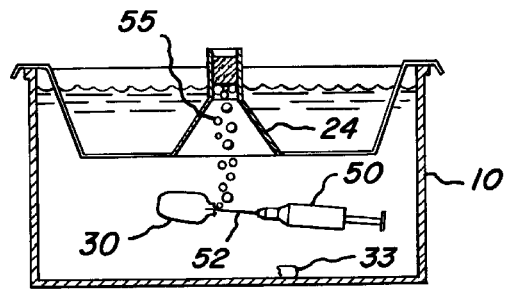
FIG. 4B shows a second process step.

FIG. 4B shows the next step of the process, whereby a water-filled syringe 50 with a hollow needle 52 is inserted into the broken opening of ampule 30 and water from the syringe 50 is injected into the interior of ampule 30. This forces entrapped gas inside ampule 30 to escape, and gas bubbles 55 migrate upwardly into the chamber 20 formed by funnel 24.

Figure 4C:
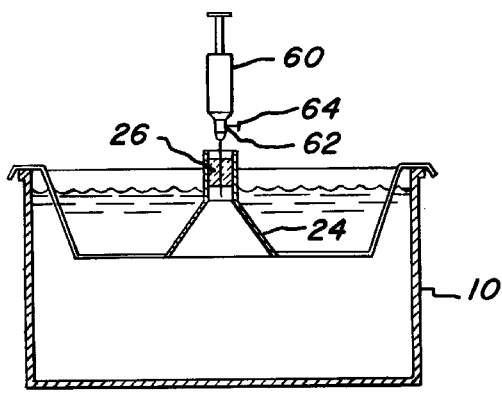
FIG. 4C shows a third process step.

FIG. 4C shows the next step of the process, wherein a syringe 60 which has been purged of air, and a hollow needle 62 is inserted through stopper 26 and into the upper portion of chamber 20. It should be noted that syringe 60 preferably has a shutoff valve 64 which remains closed until the needle 62 opening is positioned in chamber 20, and particularly into the gas region at the top of chamber 20. This gas region contains the accumulated gas bubbles 55 which were forced from the interior of ampule 30 during a previous step of the process. The gas shut-off valve 64 is then opened and the plunger of syringe 60 is withdrawn to withdraw a gas sample from chamber 20 into syringe 60. After the gas sample is withdrawn the valve 64 is again closed and the needle is withdrawn from stopper 26.

Figure 4D:
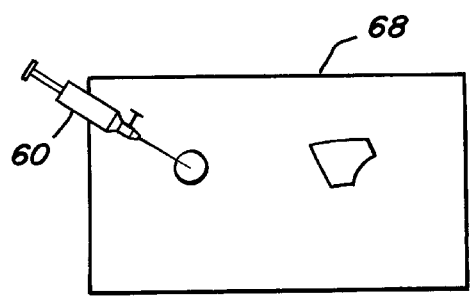
FIG. 4D shows a final process step.

FIG. 4D shows the final step of the process, wherein the gas in syringe 60 is injected into a commercially available gas analyzer machine 68. One machine which is useful for this purpose is manufactured by the assignee of the present invention and is sold under the trademark "PAC-CHECK," specifically known as a Model 450 Mocon Head Space Analyzer. This machine provides an output indication of the oxygen content of the gas which has been injected into the machine.

The present invention may be embodied in other forms of test apparatus without departing from the spirit or essential attributes of the invention; it is, therefore, desired that the present embodiment of the test apparatus be considered in all respects as illustrative and not restrictive, reference being made to the appended claims rather than to the foregoing description to indicate the scope of the invention.

What is claimed is:

1. A method for obtaining gas samples from a sealed glass ampule containing liquid and gas, comprising the steps of:
    a. immersing the sealed glass ampule in water beneath a chamber at least partially immersed in the same water and having a bottom opening immersed in the same water, the chamber being initially filled with water and completely purged of air;
    b. breaking the glass ampule beneath the bottom opening of said chamber to permit the gas in the ampule to bubble upwardly into the chamber;
    c. inserting a hollow needle into the chamber, and withdrawing a sample of the gas from the chamber, which sample comprises a sample of the gas from the glass ampule which has bubbled upwardly into said chamber.

2. The method of claim 1, comprising the further step after step (b) of injecting water into the broken glass ampule to force gas in the ampule to bubble upwardly into the chamber.

3. The method of claim 1, wherein the chamber further comprises a neck having a resilient stopper inserted therein, and the step of inserting a hollow needle further comprises inserting said hollow needle through said resilient stopper into the chamber.

4. The method of claim 3, wherein the chamber further comprises an inverted funnel, said funnel having a predetermined interior volume, and the step of bubbling the gas from the broken ampule upwardly further comprises bubbling upwardly into the predetermined interior volume defined by said inverted funnel.

5. A method of obtaining a gas sample from a sealed glass ampule containing gas and a liquid, comprising:
    a. immersing an inverted funnel having a resilient stopper in a funnel neck and having an open bottom into a container of water whereby the volume defined by the inverted funnel and funnel neck becomes completely filled with water and completely purged of air, and supporting the inverted funnel with the open bottom immersed in the water;
    b. positioning a sealed glass ampule containing liquid and gas beneath said funnel;
    c. breaking open said sealed glass ampule, thereby permitting the gas in said ampule to bubble upwardly into said funnel neck;
    d. inserting a hollow needle through said stopper into said funnel neck, said hollow needle being connected to a syringe;
    e. withdrawing a sample of gas from said funnel neck into said syringe through said hollow needle; and
    f. injecting said sample of gas from said syringe into a gas analyzer machine.

6. The method of claim 5, wherein the step of breaking open said glass ampule further comprises inserting a hollow needle connected to a syringe full of water into said glass ampule and injecting said water into said ampule.

7. The method of claim 6, wherein the step of inserting a hollow needle through said stopper further comprises inserting a hollow needle having a shut-off valve through said stopper; and opening said shut-off valve to permit gas flow through said hollow needle.

* * * * *